United States Patent
Cohen

(10) Patent No.: US 10,772,977 B2
(45) Date of Patent: Sep. 15, 2020

(54) SYSTEM AND METHOD FOR DAMAGING PARASITES

(71) Applicant: ParaSonic Ltd., Nazareth (IL)

(72) Inventor: Mor Miri Cohen, Ramat-Gan (IL)

(73) Assignee: ParaSonic Ltd., Nazareth (IL)

( * ) Notice: Subject to any disclaimer, the term of this patent is extended or adjusted under 35 U.S.C. 154(b) by 0 days.

(21) Appl. No.: 16/157,403

(22) Filed: Oct. 11, 2018

(65) Prior Publication Data

US 2019/0038786 A1 Feb. 7, 2019

Related U.S. Application Data

(63) Continuation of application No. 14/000,887, filed as application No. PCT/IL2012/050058 on Feb. 23, 2012, now Pat. No. 10,105,457.

(60) Provisional application No. 61/446,589, filed on Feb. 25, 2011, provisional application No. 61/493,422, filed on Jun. 4, 2011.

(51) Int. Cl.

| | |
|---|---|
| *A61L 2/025* | (2006.01) |
| *A01K 13/00* | (2006.01) |
| *A45D 24/30* | (2006.01) |
| *A61N 7/00* | (2006.01) |
| *A46B 15/00* | (2006.01) |
| *A61K 8/33* | (2006.01) |
| *A61K 8/34* | (2006.01) |
| *A61K 8/40* | (2006.01) |
| *A61K 8/43* | (2006.01) |
| *A61K 8/44* | (2006.01) |
| *A61Q 17/02* | (2006.01) |

(52) U.S. Cl.
CPC ............ *A61L 2/025* (2013.01); *A01K 13/002* (2013.01); *A01K 13/003* (2013.01); *A45D 24/30* (2013.01); *A46B 15/0028* (2013.01); *A61K 8/33* (2013.01); *A61K 8/347* (2013.01); *A61K 8/40* (2013.01); *A61K 8/43* (2013.01); *A61K 8/44* (2013.01); *A61N 7/00* (2013.01); *A61Q 17/02* (2013.01); *A45D 2200/207* (2013.01); *A46B 2200/104* (2013.01); *A46B 2200/1093* (2013.01); *A61K 2800/82* (2013.01); *A61N 2007/0034* (2013.01)

(58) Field of Classification Search
CPC .............................. A61L 2/025; A45D 24/30
See application file for complete search history.

(56) References Cited

U.S. PATENT DOCUMENTS

| | | | |
|---|---|---|---|
| 5,297,512 A * | 3/1994 | Sharp | A01K 13/002 119/602 |
| 2010/0113983 A1* | 5/2010 | Heckerman | A61B 17/22004 601/2 |

\* cited by examiner

*Primary Examiner* — Donald R Spamer
(74) *Attorney, Agent, or Firm* — Greenberg Traurig, LLP

(57) ABSTRACT

A method of damaging a parasite while being a resident in or on a surface of a body of a mammal. The method comprises irradiating the parasite with ultrasound radiation at a frequency of from about 1 MHz to about 2.6 MHz for a period of at last one second.

11 Claims, 10 Drawing Sheets

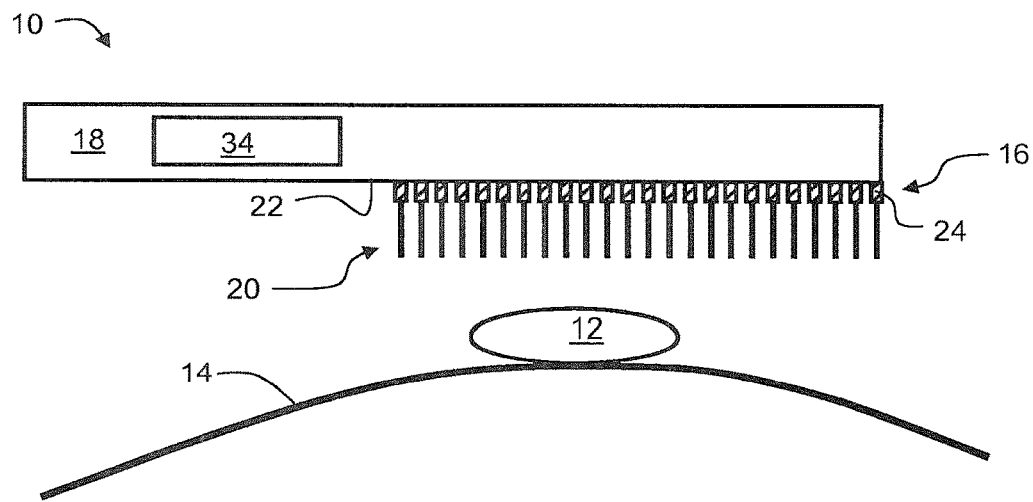
FIG. 3
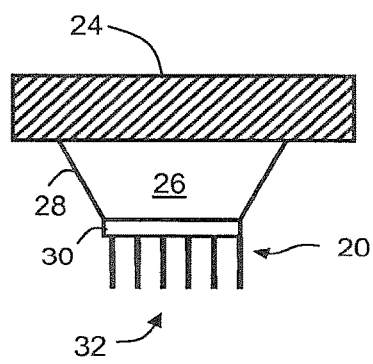 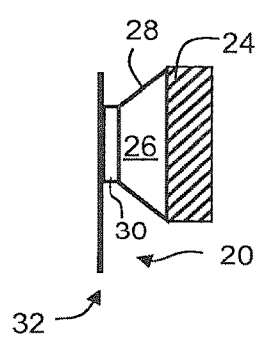 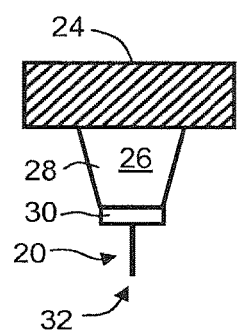
FIG. 4A      FIG. 4B      FIG. 4C FIG. 10
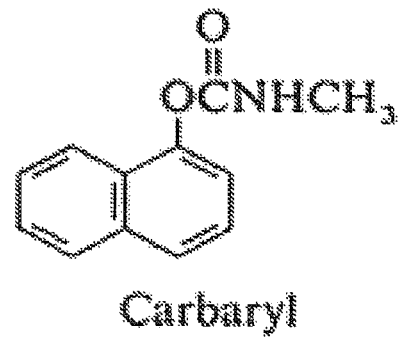
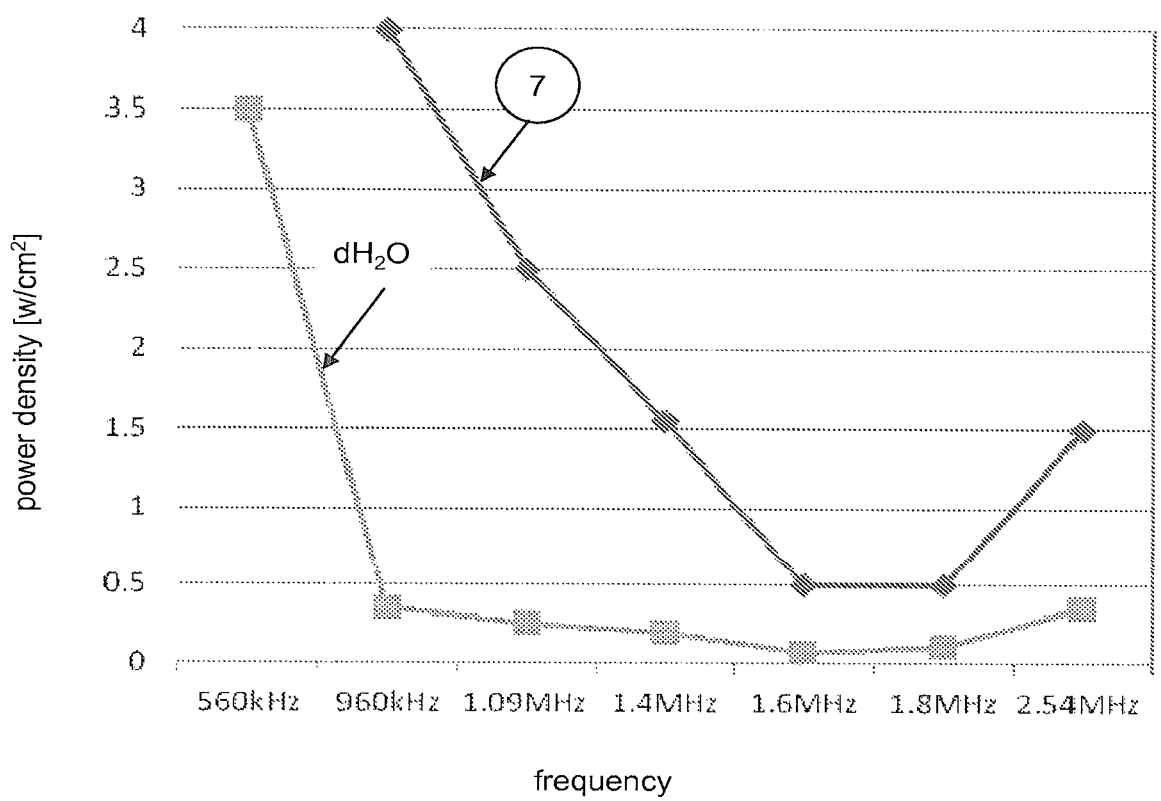
FIG. 11

SYSTEM AND METHOD FOR DAMAGING PARASITES

RELATED APPLICATIONS

This application is a continuation of U.S. patent application Ser. No. 14/000,887, filed Aug. 22, 2013, entitled "SYSTEM AND METHOD FOR DAMAGING PARASITES", which is a National Phase Application of PCT International Application No. PCT/IL2012/050058, International Filing Date Feb. 23, 2012, entitled "SYSTEM AND METHOD FOR DAMAGING PARASITES", which claims the benefit of priority of U.S. Provisional Patent Application No. 61/446,589 filed Feb. 25, 2011, and 61/493,422 filed Jun. 4, 2011, the contents of which are incorporated herein by reference in their entirety

FIELD AND BACKGROUND OF THE INVENTION

The present invention, in some embodiments thereof, relates to parasite destruction and, more particularly, but not exclusively, to a system and method for damaging parasites and optionally parasite eggs by ultrasound.

Parasitic sucking lice feed on the blood, serum or lymph of their hosts and cause irritation, pruritis and disease. Some species are vectors of serious diseases and all are generally undesirable. For example, the common human head louse, *Pediculus capitis* and the human pubic louse *Phthirus pubis* are blood sucking ectoparasites which cause pediculosis disease, producing hives like irritation and pruritis in infested subjects. The human body louse, *Pediculus humanus corporis* causes irritation and pruritis and is also a vector of typhus, which is a potentially lethal disease.

Head lice are a common problem, particularly among children and are highly 20 communicable. Head lice attach to hair, move to the scalp where they become resident and feed on the blood. Lice may pierce the skin and exude an antigenic salivary secretion which, with the piercing of the skin, creates a pruritic dermatitis.

The head lice lay eggs (also known as nits), which become attached to hairs close to the scalp by a drop of cement secreted by the female louse, which subsequently becomes hard. Female lice lay 50-150 eggs in their lives. Upon sufficient growth, the eggs hatch thereby increasing the numbers of lice on the scalp. If not treated, the amount of lice on the head of an individual may become substantial and pose a serious health risk.

Once a significant number of lice get a foothold in the scalp of a human, they are extremely difficult to eradicate. Heretofore, various attempts have been made to treat people with head lice. These include anti-lice substances and shampoos, and nonpharmacologic approaches including occlusion therapy, nit combing, and hair removal.

A device for mechanically removing and killing lice is marketed under the trade name Lice-Guard Robi® Comb (Epilady® 2000, L.L.C.). The device is a battery-powered electronic comb with oscillating tooth that electrocute lice.

U.S. Pat. No. 5,318,051 describes a fine tooth comb with an electric power source. The comb includes two sections formed of conductive sheet material which are insolated from each other by an insulating separator. The comb also includes two interleaved sets of teeth, each extending from one of the sections. An electric potential applied between adjacent teeth causes current to flow through an intervening nit.

U.S. Published Application No. 2002096125 describes a hair grooming comb, such as for pet, with ionizer for ionized air onto hair to be groomed and with an ultrasonic wave generator for generating ultrasonic waves onto hair in order to repel fleas. The used comb is a brush that goes thought the fur and does not create a closed acoustic filed, therefore the apparatus is only using for repealing fleas.

Chinese Patent No. 2843056 describes an ultrasonic insect-repelling massage comb, which comprises comb teeth, a comb handle and an outer shell. A pet vibration comb emit sound wave frequency, exceeds the hearing range of human and pet, for expelling fleas, louses, etc. As the person' skilled in the art will appreciate, if a teeth comb emits ultrasonic wave with no appropriate mediate, the ultrasonic wave will not be effective since ultrasound is poorly pass troughs air.

International Publication Nos. 2007/037143 and 2009/107034 describe an ultrasonic hair treatment device having clamps with a vibrator. Impregnation and infusion hair treatment agent is accelerated into the hair and distributed therein by ultrasonic vibration.

Additional background art includes Douglas L Miller, Progress in Biophysics and Molecular Biology (2007), 93 (1-3): 314-330; Child et al., 1980, Ultrasound in Medicine and Biology, 6(2):127-130; Child et al., 1981, Ultrasound in Medicine and Biology 7(2):167-173; Child et al., 1982, Pay et al., 1987, Ultrasound in Medicine and Biology 13(2):93-95. These publications describe various studies directed to investigate the effect of ultrasound on mammalian tissue and *Drosophila melanogaster.*

SUMMARY OF THE INVENTION

According to an aspect of some embodiments of the present invention there is provided a method of damaging a parasite while being a resident in or on a surface of a body of a mammal. The method comprises irradiating the parasite with ultrasound radiation at a frequency of from about 1 MHz to about 2.6 MHz for a period of at least one second.

According to an aspect of some embodiments of the present invention there is provided a system for damaging a parasite while being a resident in or on a surface of a body of a mammal. The system comprises an ultrasound transmitter, configured for generating ultrasound radiation at a frequency of from about 1 MHz to about 2.6 MHz for a period of at least one second; and a hand-held device coupled to the ultrasound transmitter and adapted for being placed on or at proximity to the parasite so as to deliver the ultrasound radiation to the parasite.

According to some embodiments of the invention the parasite comprises a head louse. According to some embodiments of the invention the parasite comprises a nit.

According to some embodiments of the invention the frequency is from about 1.4 MHz to about 2.6 MHz. According to some embodiments of the invention the frequency is from about 1.4 MHz to about 1.8 MHz. According to some embodiments of the invention the frequency is from about 1.5 MHz to about 1.8 MHz. According to 20 some embodiments of the invention the frequency is from about 1.53 MHz to about 1.8 MHz. According to some embodiments of the invention the frequency is from about 1.6 MHz to about 1.8 MHz According to some embodiments of the invention the ultrasound transmitter is configured for providing a power density of at most 0.5 W/cm2. According to some embodiments of the invention the ultrasound transmitter is configured for providing a power density of at most $0.35 \text{ W/cm}^2$.

According to some embodiments of the invention the ultrasound transmitter is configured for providing a power density of at least 0.08 W/cm².

According to some embodiments of the invention the irradiating is in the 30 presence of an impedance matching medium.

According to some embodiments of the invention the irradiating is executed while the parasite is in direct contact with an ultrasound transmitter generating the ultrasound radiation.

According to some embodiments of the invention the irradiating is in the presence of a liquid composition having an active agent.

According to some embodiments of the invention the liquid composition is selected such as to provide at least partial impedance matching between a body of the parasite and a body of an ultrasound transmitter emitting the radiation and the parasite.

According to some embodiments of the invention the liquid composition is non-toxic to the parasite in the absence of the ultrasound radiation.

According to some embodiments of the invention the liquid composition comprises an antimicrobial agent.

According to some embodiments of the invention the liquid composition comprises a pesticide.

According to some embodiments of the invention the liquid composition comprises silica.

According to some embodiments of the invention the liquid composition comprises EDTA.

According to some embodiments of the invention the liquid composition comprises silica and EDTA.

According to some embodiments of the invention the concentration of silica is from about 0.1 wt. % to about 5 wt. %. According to some embodiments of the invention the concentration of silica is from about 0.25 wt. % to about 5 wt. %. According to some embodiments of the invention the concentration of silica is from 25 about 0.5 wt. % to about 5 wt. %. According to some embodiments of the invention the concentration of silica is from about 0.25 wt. % to about 3 wt. %. According to some embodiments of the invention the concentration of silica is from about 0.25 wt. % to about 2 wt. %. According to some embodiments of the invention the concentration of silica is about 0.5 wt. %. According to some embodiments of the invention the concentration of silica is about 1 wt. %. According to some embodiments of the invention the concentration of silica is about 2 wt. %. According to some embodiments of the invention the concentration of silica is about 3 wt. %.

According to some embodiments of the invention the EDTA is at molarity of from 0.05 to 0.5.

According to some embodiments of the invention the EDTA is at molarity of from about 0.05 to about 0.2. According to some embodiments of the invention the 5 EDTA is at molarity of from about 0.05 to about 1.5. According to some embodiments of the invention the EDTA is at molarity of 0.1.

According to some embodiments of the invention the method comprises removing the parasite from the body subsequently to the irradiation.

According to some embodiments of the invention the removal is effected by vacuum.

According to some embodiments of the invention the removal is effected by combing.

According to some embodiments of the invention the hand-held device comprises a comb having a plurality of teeth extending from a base.

According to some embodiments of the invention the ultrasound transmitter comprises a vibrating element mounted on the base so as to collectively vibrate the teeth.

According to some embodiments of the invention the ultrasound transmitter comprises a plurality of vibrating elements each being mounted on a different tooth so as to vibrate the tooth.

According to some embodiments of the invention the ultrasound transmitter comprises a plurality of vibrating elements mounted on the base, and wherein each tooth of the plurality of teeth is mounted on a different vibrating element and being vibrated thereby.

According to some embodiments of the invention the hand-held device comprises a gripping device.

According to some embodiments of the invention the gripping device comprises a pair of pivotally attached arms biasable towards each other.

According to some embodiments of the invention the pair of arms comprises a first arm having a base and a plurality of teeth extending from the base.

According to some embodiments of the invention the pair of arms comprises a second arm being devoid of teeth.

According to some embodiments of the invention the pair of arms comprises a second arm having a base and a plurality of teeth extending from the base, and where when the arms are biased towards each other, the plurality of teeth of the first arm is interlaced with the plurality of teeth of the second arm.

According to some embodiments of the invention the hand-held device comprises a hollow member having a body portion and a head portion, the body portion having an open end adapted to be coupled to a vacuum hose and the head portion having an opening defining an intake for capturing the parasite.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings.

With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of a system for damaging a parasite according to some embodiments of the present invention;

FIG. 2 is a schematic illustration of a system for damaging a parasite in embodiment of the invention in which the ultrasound transmitter comprises a plurality of 30 vibrating elements each being mounted on a different tooth;

FIG. 3 is a schematic illustration of a system for damaging a parasite in embodiment of the invention in which the vibrating elements are mounted on a base and each tooth is mounted on a different vibrating element;

Figure 6:
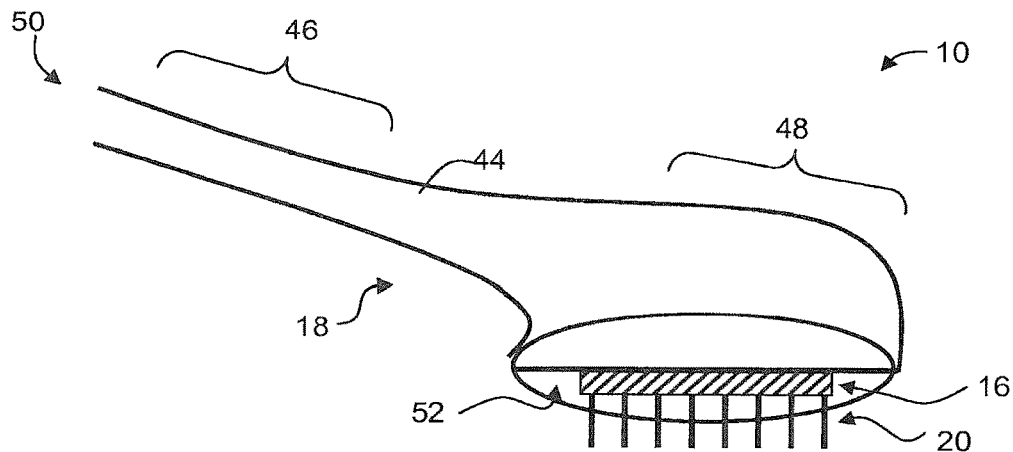
Figure 7:
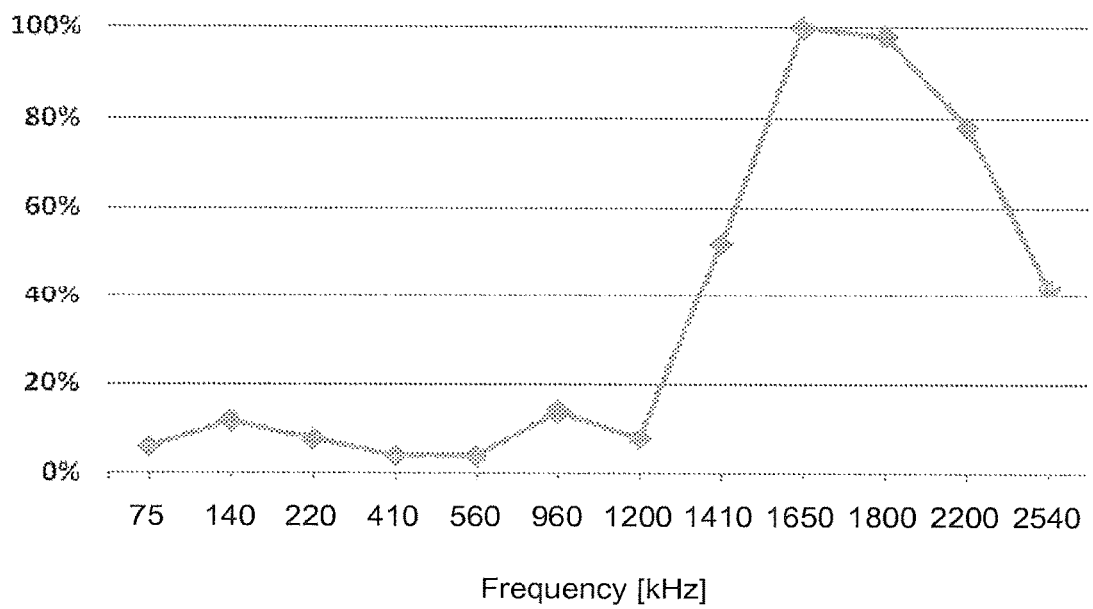
Figure 9:
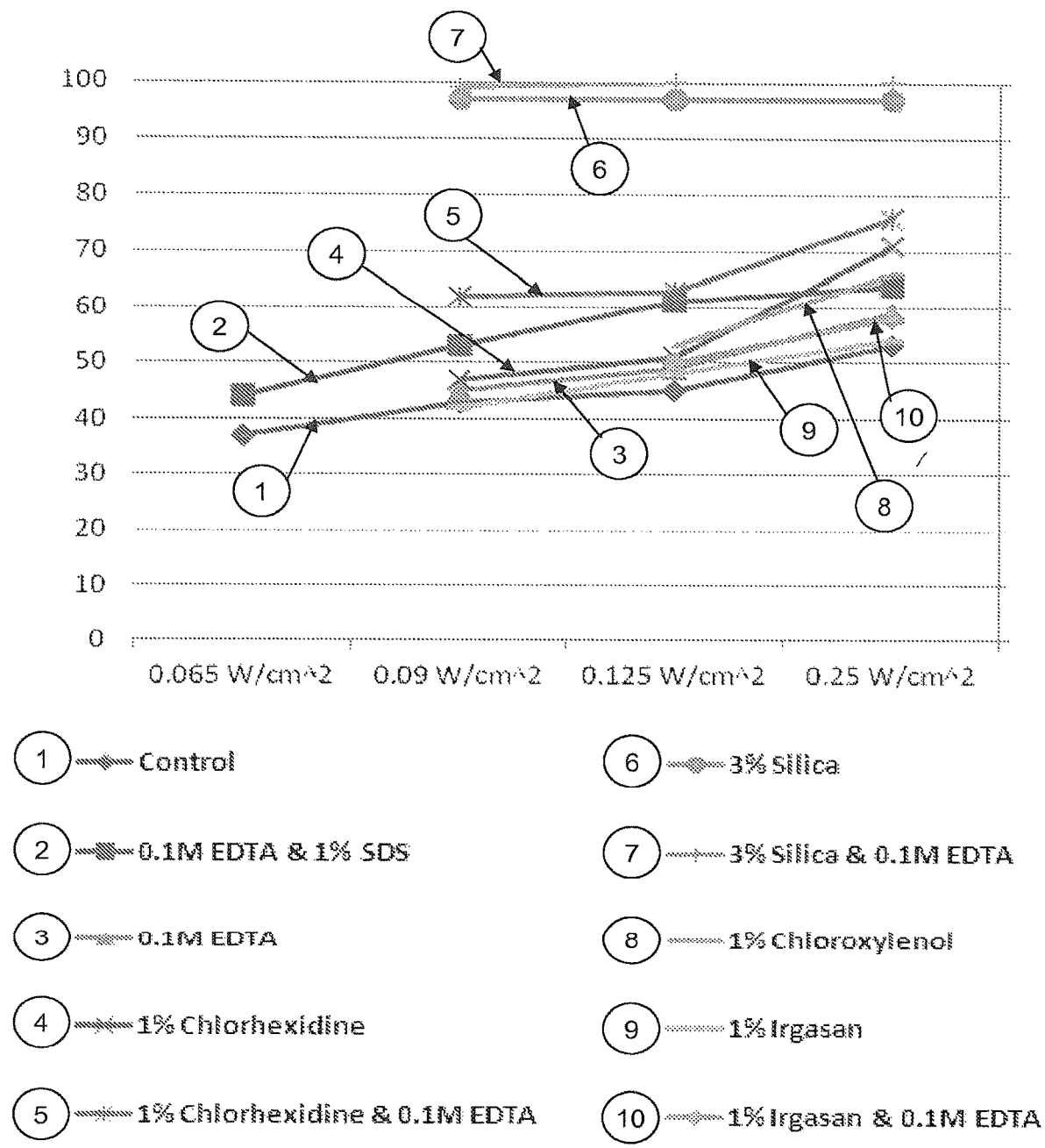

FIGS. 4A-C are schematic illustrations of an acoustic amplifier, according to some embodiments of the present invention;

FIGS. 5A-G are schematic illustrations showing various configurations of a hand-held according to some embodiments of the present invention;

FIG. 6 is a schematic illustration of a system for damaging a parasite according to embodiments of the invention in which the system comprises a hollow member for removing the parasite by vacuum;

FIG. 7 is a graph showing the mortality in percentage as a function of the frequency in kHz, as obtained during experiments performed according to some embodiments of the present invention;

FIGS. 8A-D are schematic illustrations of chemical agents used in experiments performed according to some embodiments of the present invention;

FIG. 9 is a graph showing the mortality in percentage as a function of the power density, for various types of active agents, as obtained during experiments performed according to some embodiments of the present invention;

FIG. 10 is a schematic illustration of another chemical agent used in experiments performed according to some embodiments of the present invention; and FIG. 11 is a graph showing a power density at which at least 90% mortality was achieved, as a function of the frequency, as obtained during experiments performed according to some embodiments of the present invention.

DESCRIPTION OF SPECIFIC EMBODIMENTS OF THE INVENTION

The present invention, in some embodiments thereof, relates to parasite destruction and, more particularly, but not exclusively, to a system and method for damaging parasites and optionally parasite eggs by ultrasound.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

According to some embodiments of the present invention, there is provided a method suitable damaging a parasite while being a resident in or on a surface of a body of a mammal. The parasite can be of any type that typically becomes resident, at least temporarily, in or on the skin of the mammal. Representative examples include, without limitation, lice, louse eggs (also known as nits), ticks, fleas, biting insects, true bugs, mites, bedbugs and other pests. In some embodiments of the invention the parasite is a louse and in some embodiments of the present invention the parasite is a nit.

The parasite can be located at any part of the body. Typically, the parasite is located at a hairy or furry part of the body. For example, when the parasite is a louse or a nit, it can be located on the head of a human, e.g, a child.

The method typically comprises irradiating the parasite with ultrasound radiation, wherein at least one of a frequency, a duration and power of the ultrasound radiation is selected to damage the parasite.

As used herein "damage" refers to a process in which the viability of the parasite is at least partially reduced.

Preferably, the ultrasound radiation is selected to kill the parasite. When the parasite is a nit or an egg, the ultrasound radiation is optionally and preferably selected to destroy the ability of the nit or egg to hatch. In various exemplary embodiments of the invention the ultrasound radiation is selected such as not to induce cavitation near or in the parasite.

Typical ultrasound frequencies suitable for the present embodiments including, without limitation, from about 1 MHz to about 2.6 MHz, or from about 1.4 MHz to 2.6 MHz, or from about 1.4 MHz to about 1.8 MHz, or from about 1.5 MHz to about 1.8 MHz, or from about 1.53 MHz to about 1.8 MHz. In experiments performed by the present inventor, it was found that the above ranges of frequencies are particularly useful for killing lice. Other frequencies, however, are not excluded from the scope of the present invention.

Typically, but not necessarily, the irradiation is applied for a period of one or more seconds, e.g, for a period of from about 1 second to about 4 seconds, or from about 1 second to about 3 seconds, or from about 1 second to about 2 seconds. Other periods, for example, less than one second or more than 4 seconds are also contemplated.

The power density of the ultrasound radiation at the emitting face of the ultrasound transmitter is preferably 3 W/cm$^2$ or less, more preferably 2 W/cm$^2$ or less, more preferably 1 W/cm$^2$ or less, more preferably 0.5 W/cm$^2$ or less. In various exemplary embodiments of the invention the density of the ultrasound radiation at the emitting surface of the ultrasound transmitter is at least 0.08 W/cm$^2$.

The irradiation by ultrasound can be executed while the parasite is in direct contact with the ultrasound transmitter generating the radiation. Alternatively, the irradiating can be in the presence of an impedance matching medium. The impedance matching medium can be of any type and form. Preferably, the acoustic impedance of the medium is between the characteristic acoustic impedance of the emitting face of the ultrasound transmitter and the characteristic acoustic impedance of the parasite's body.

In some embodiments, the irradiation is in the presence of a liquid composition having an active agent. The liquid composition can be selected such as to provide at least partial impedance matching between the body of parasite and the emitting face of the ultrasound transmitter.

In some embodiments, the composition is non-toxic to the parasite in the absence of the ultrasound radiation. It was found by the present inventor that even such compositions are suitable for damaging the parasite when combined with ultrasound radiation. Without wishing to be bound to any particular theory, it is assumed that in the absence of ultrasound radiation, when the cuticle of the parasite is intact, the liquid composition contacts the parasite only externally and there is no systemic exposure to the agent. Such external contact is insufficient for reducing the viability or vitality of the parasite. On the other hand, when the liquid composition is used in combination with the ultrasound radiation of the present embodiments, the ultrasound radiation wounds the cuticle of the parasite, thereby allowing systemic delivery of the active agent into the parasite through the wound. Once the agent systemically contacts the parasite, the parasite is damaged.

Thus, the active agent is optionally and preferably toxic to parasite when systemically contacting the parasite. For example, the active agent can be an antimicrobial agent.

As used herein, "antimicrobial agent" refers to any agent that kills, inhibits the growth of, or prevents the growth of a bacteria, fungus, yeast, or virus.

Antimicrobial agents suitable for the present embodiments include pharmaceutical agents, biocidal or pesticidal agents (e.g, insecticides, herbicides, and rodentacides), antibacterial agents, antifingal agents, and antiviral agents.

Exemplary active agents that are toxic when systemically contacting the parasite include, but are not limited to, salts of alkali metals, such as, but not limited to, sodium chloride (NaCl), sodium fluoride (NaF), calcium chloride ($CaCl_2$), magnesium chloride ($MgCl_2$), barium chloride ($BaCl_2$) and the like; fluoride-containing silicates or aluminates, such as sodium fluorosilicate, barium fluorosilicate, sodium fluoroaluminate and the like, each containing one or more fluoride group(s); carboxylic acids such as citric acid and acetic acid, and any additional agent that has an insecticidal or pecticiadal activity, including carbaryl (1-naphthyl methylcarbamate) and derivatives thereof, polyethylene imine, urea derivatives thereof and EDTA.

Additional exemplary agents include biocides, such as, but not limited to, chlorhexidine, chlorhexidine gluconate, chlorhexidine acetate, chlorhexidine hydrochloride, dibromopropamidine, halogenated diphenylalkanes, dibromsalan, metabromsalan, tribromsalan, carbanilide, salicylanilide, tetrachlorosalicylanilide, trichlorocarbanilide, propamidine isethionate, pentamidine, picloxydine, mendalamine,20 the acid addition and quaternary, methenaminc mandelate, polyoxymethylene esters such as polyoxymethylene diester, polyoxymethylene diacetate and the like, and mixtures thereof. Also contemplated is one or more biocide selected from the group consisting of triclosan, chlorhexidine dihydrochloride, chlorhexidine gluconate, chlorhexidine acetate, chlorhexidine diacetate, chloroxylenol, dequalinium chloride, benzethonium chloride, benzalkonium chloride and combinations thereof.

In some embodiments of the present invention the active agent is selected so as to maintain or at least reduce the recovery rate of the wound caused by the ultrasound radiation. For example, it was found by the present inventor that the combination of 3% silica and 0.1M EDTA, is useful in maintaining wounds formed on louse bode open.

In some embodiments of the present invention the parasite is removed from the body subsequently to the irradiation. This can be done by any technique known in the art, including, without limitation, washing, combing and application of vacuum.

Figure 1:
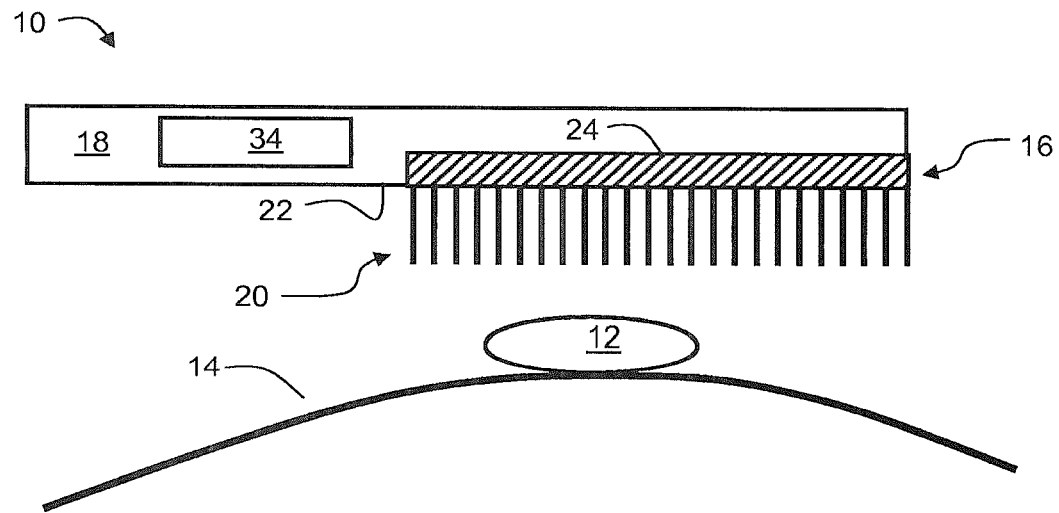

Reference is now made to FIG. 1 which is a schematic illustration of a system 10 for damaging a parasite 12 while being a resident in or on a surface 14 of a body of a mammal. System 10 comprises an ultrasound transmitter 16 having a vibrating element 24, configured for generating ultrasound radiation as further detailed hereinabove. Ultrasound transmitter 16 can be embodied in the form of an electromechanical transducer in which vibrating element 24 is typically a piezoelectric element.

In some embodiments of the present invention system 10 also comprises a hand-held device 18 coupled to ultrasound transmitter 16 and being adapted for being placed on or at proximity to parasite 12 so as to deliver ultrasound radiation to parasite 12. Device 18 can include electronic circuitry 34 for controlling the operation of ultrasound transmitter 16. Device 18 is preferably mobile and powered by an independent power source, e.g, a battery (not shown). Alternatively, device 18 can include a power cord (not shown) for connecting device 18 to an external power source.

The present inventor contemplates many configurations for hand-held device 18, and the relation between device 18 and transmitter 16. In the representative example shown in FIG. 1, device 18 comprises a comb having a plurality of teeth 20 extending from a base 22. In this illustration, the vibrating element of ultrasound transmitter 16 is mounted on base 22 so as to collectively vibrate teeth 20.

Use of teeth 20 is particularly useful when system 10 is operated for damaging a parasite residing on a hairy or furry surface of the mammal. For example, teeth 20 can be useful for damaging head lice and/or nits, in which case the irradiation by ultrasound radiation is accompanied by hair combing for facilitating the removal of the lice and/or nits from the hair. In some embodiments of the present invention the spacing between adjacent teeth is selected to allow passage of a hair shaft between adjacent teeth, but prevents passage of lice and nits. For example, the spacing between adjacent teeth can be from about 1 mm to about 3 mm. However, this need not necessarily be the case, since, for some applications, it may be sufficient to have larger spacing.

Figure 2:
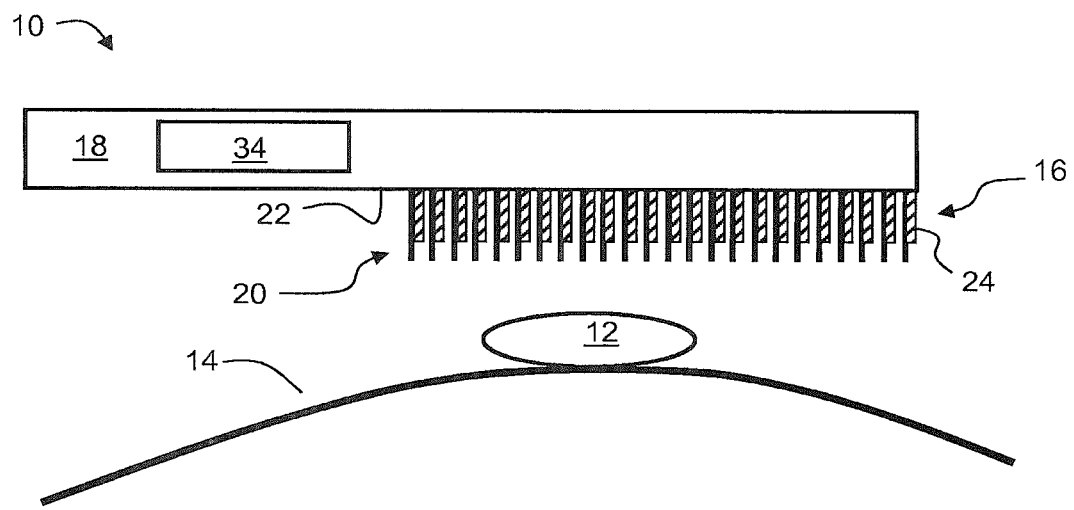

FIG. 2 is a schematic illustration of system 10 in embodiment of the invention in which ultrasound transmitter 16 comprises a plurality of vibrating elements 24 each being mounted on a different tooth of so as to vibrate the respective tooth.

FIG. 3 is a schematic illustration of system 10 in embodiment of the invention in which vibrating elements 24 are mounted on base 22 and each tooth is mounted on a different vibrating element, such that the respective vibrating element vibrates the respective tooth.

In some embodiments of the present invention system 10 amplifies the amplitude of the acoustic waves carrying the acoustic energy. This can be done, for example, 5 using an acoustic amplifier which is configured for amplifying the amplitude of acoustic waves prior to the coupling of acoustic energy into teeth 20.

A representative example of an embodiment in which system 10 comprises acoustic amplifier 26 is illustrated in FIGS. 4A-C. Acoustic amplifier 26 can comprise an acoustic horn, which is constructed to receive vibrations from the vibrating element 24 and transmit the vibrations to teeth 20. Preferably, the horn is tapered toward the teeth. The horn may be provided with a tapered wall portion 28 and a tip 30, which may be cylindrical, however, this need not necessarily be the case since other configurations are contemplated as well. The tapered wall portion 28 may be frustoconical, however, however, this need not necessarily be the case since other configurations are contemplated as well, such as for example, elliptical, conical, bi-conic, parabolic and stepped.

FIG. 4A illustrates a configuration in which the same acoustic amplifier transmits the vibrations to several teeth 20, wherein the vibrations are generally along the longitudinal axis of the teeth. This embodiment is particularly useful for a configuration in which vibrating element 24 is mounted on base 22 (not shown in FIG. 4A, see e.g, FIG. 1) so as to collectively vibrate several teeth 20.

FIG. 4B illustrates a configuration in which an acoustic amplifier transmits the vibrations to one tooth, wherein the vibrations are generally perpendicular (e.g., at an angle of 70° or more) to the longitudinal axis of the teeth. This embodiment is particularly useful for a configuration in which the ultrasound transmitter comprises a plurality of vibrating elements. Thus, each tooth can be coupled along its length to a respective acoustic amplifier which is mounted between the respective tooth and the respective vibrating element.

FIG. 4C illustrates a configuration in which an acoustic amplifier transmits the vibrations to one tooth, wherein the vibrations are generally along the longitudinal axis of the tooth. This embodiment is particularly useful for a configuration in which there is a plurality of vibrating elements mounted on base 22 (not shown in FIG. 4C, see e.g, FIG. 3). Thus, for each vibrating element there can be a respective amplifier mounted thereon, wherein the tip of each tooth is coupled to the respective acoustic amplifier.

Optionally and preferably, the amplitude of the vibrations are further amplified by the teeth themselves. This can be done, for example, by providing teeth 20 with sufficient flexibility and elasticity such that the amplitude of the vibrations is enhanced by an elastic resonance effect. Optionally, the amplitude of the vibrations at the distal ends 32 of teeth 20 is larger than the amplitude of the vibrations of element 24 and amplifier 26.

Other configurations of hand-held device 18 are schematically illustrated in FIGS. 5A-G. In the configurations shown in FIGS. 5A, 5B, 5E, 5F and 5G, hand-held device 18 comprises a gripping device 36. Generally, gripping device 36 comprises a pair of pivotally attached arms 40, 42 having respective gripping portions 60, 62 biasable towards each other. Gripping device 36 can be configured for gripping the parasite itself, or an object near the parasite or an on which the parasite resides. For example, when system 10 is employed for damaging lice and/or nits, gripping device 36 can be configured for gripping hairs, preferably near the scalp.

Figure 5A:
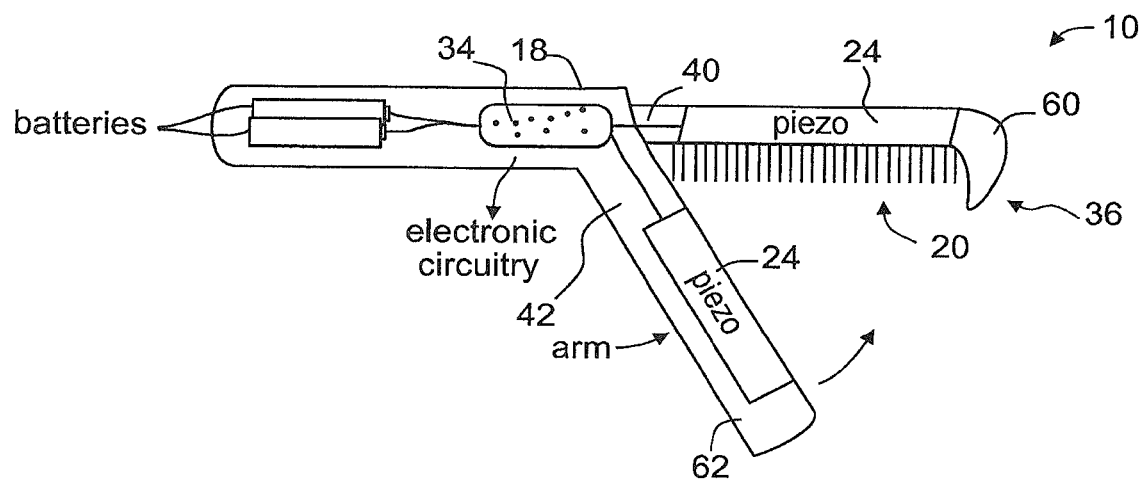
Figure 5B:
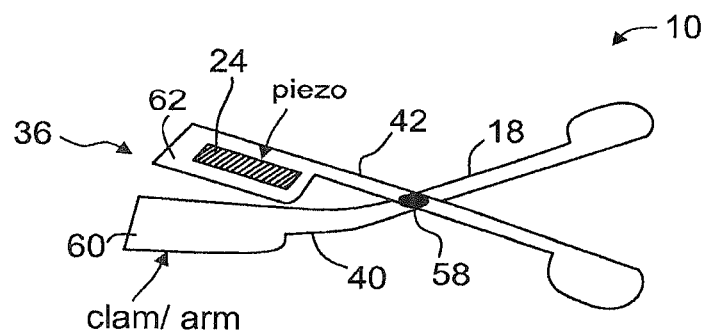
Figure 5C:
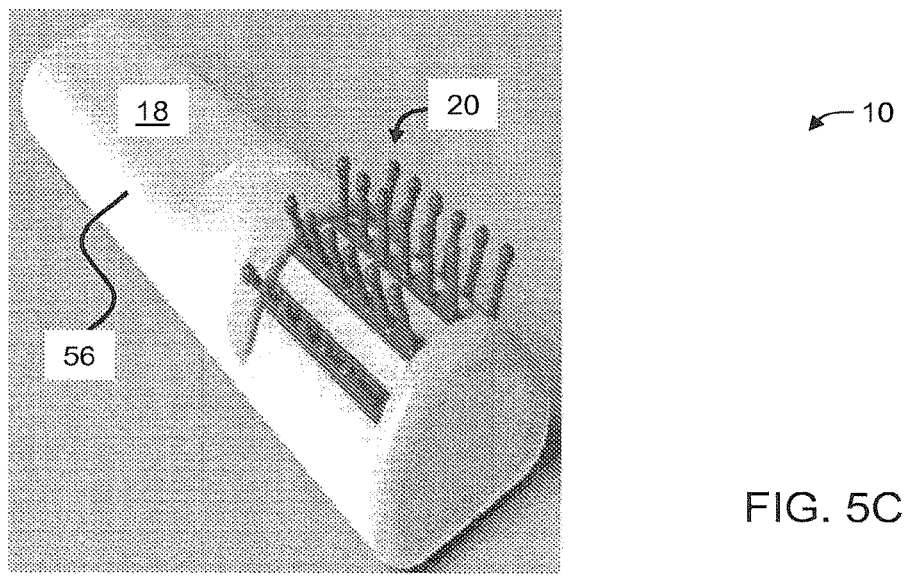
Figure 5D:
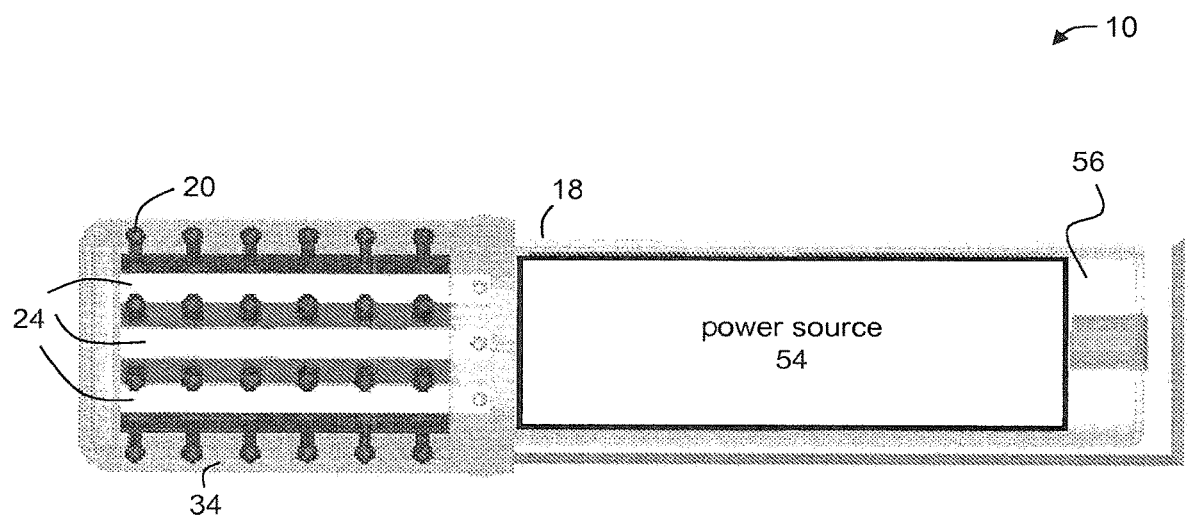
Figure 5E:
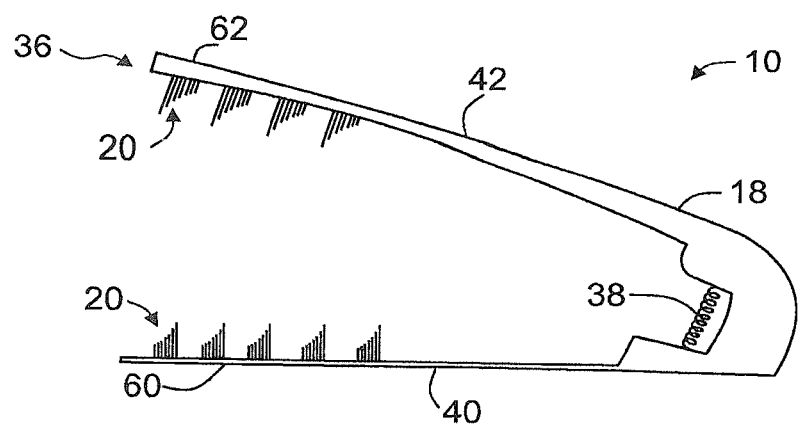
Figure 5F:
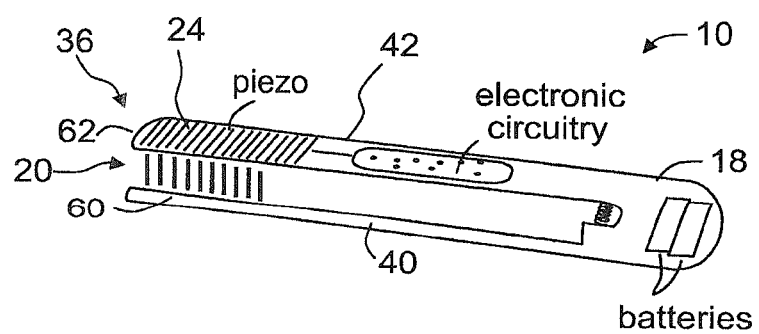

In the representative illustrations of FIGS. 5B, 5E and 5F, one of the gripping ends (gripping end 62 in the present example) receives the vibrations from vibrating element 24, while the other gripping end (gripping end 60 in the present example) is static. In the representative illustration of FIG. 5A, both griping ends are provided with vibrating elements, hence vibrate. In the representative illustration of FIG. 5G, two vibrating elements 24 serve as two respective griping arms.

In some embodiments of the present invention gripping device 36 is provided with teeth 20 (see FIGS. 5A, 5E and 5F). The teeth can be provided on one of the arms, e.g, arm 40, wherein the other arm, e.g, arm 42 is devoid of teeth (FIG. 5A). Alternatively, both arms 40 and 42 can be provided with teeth. The latter embodiment is illustrated in FIGS. 5E and 5F, where FIG. 5E shows arms 40 and 42 in an unbiased (open) state, and FIG. 5F shows arms 40 and 42 once biased against each other. Optionally and preferably the teeth of arm 40 are interlaced with the teeth of arm 42.

Figure 5G:
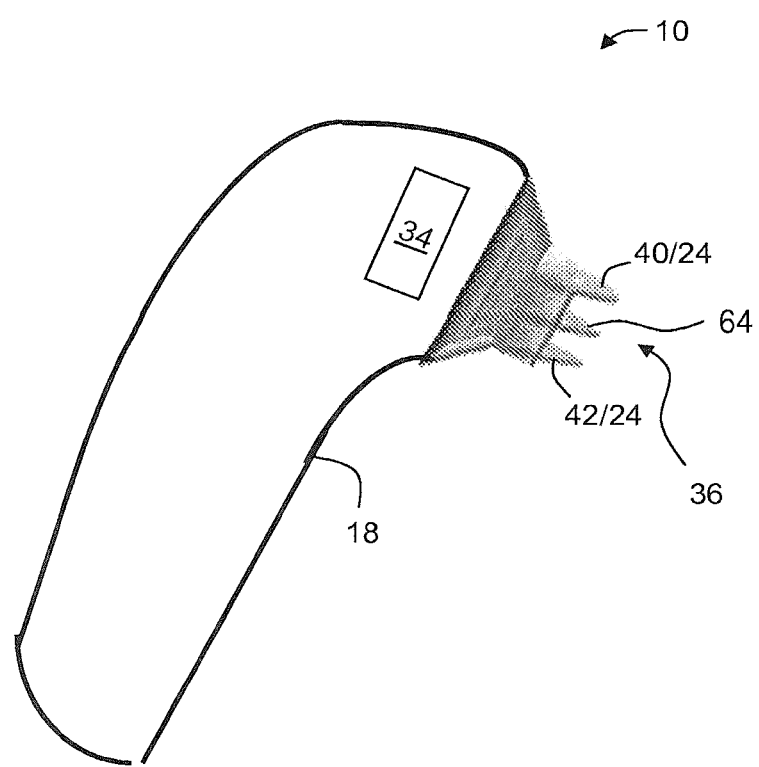

It is to be understood, however, that it is not necessary for gripping device 36 to include teeth. In some embodiments of the present invention, both arms 40 and 42 are devoid of teeth. A representative example of these embodiments is illustrated in FIGS. 5B and 5G. In FIG. 5B, gripping device 36 has a shape of scissors, wherein arms 40 and 42 are pivotally mount to each other on an axis 58 in a crossed configuration. In FIG. 5G, gripping device 36 comprises two vibrating elements 24 which may also serve as the arms 40 and 42 of the gripping device. Optionally, device 36 also comprises a plate 64 between arms 40 and 42. Plate 64 can be, for example, a metal plate. In an embodiment of the invention, plate 64 is made of aluminum.

The biasing of arms 40 and 42 towards each other can be performed manually or it can be controlled by the electronic circuitry 34. In some embodiments of the present invention gripping device 36 comprises a spring member 38 for maintaining arms 40 and 42 in an unbiased state when system 10 is not operative. This configuration is illustrated in FIG. 5E. Alternatively, spring member 38 can be constituted for maintaining arms 40 and 42 in a biased state when system 10 is not operative.

When gripping device 36 is used for damaging a parasite residing on a hairy or fury surface, gripping device 36 can be brought into proximity to the surface such that the hair or fur is positioned between arms 40 and 42. Thereafter, are biased towards each other to grip the hair or fur. Vibrating element 24 is activated prior to or immediately subsequently to the gripping. The gripping force is optionally sufficiently strong to maintain the gripped objects therein, and yet sufficiently weak to allow a relative motion (e.g, sliding) between the gripped objects and the arms of device 36. Thus, while element 24 transmits the ultrasound griping device 36 can be pulled along the gripped objects, such that the objects slides along the surfaces of arms 40 and 42. During this motion, a parasite residing on the gripped objects comes into contact with the arms hence being irradiated by the ultrasound radiation, as further detailed hereinabove.

FIGS. 5C and 5D are schematic illustrations showing a perspective view (FIG. 5C) and a cross sectional view (FIG. 5D) of system 10 in embodiments of the invention in which hand-held device is shaped as a brush, e.g, adapted for brushing hair or fur. In these embodiments teeth are arranged at any arrangement other than along a single straight line. In the representative example shown in FIGS. 5C and 5D, teeth 20 are arranged in four straight rows, but this need not necessarily be the case, since, for some applications, it may be desired to have the teeth arranged in more than four rows or less than four rows, or to be arranged not in rows (e.g, randomly). Optionally, each teeth row vibrates by means of one or more vibrating element 24 mounted under the row or between teeth rows. In the representative example illustrated in FIGS. 5C and 5D, system 10 comprises three vibrating elements each being mounted between a pair of adjacent teeth rows. The vibrating element(s) can be powered by a power source 54 that can be placed, for example, in a handle 56 of hand-held device 18, as schematically illustrated in FIG. 5D. The gaps between adjacent teeth in the brush are not necessarily fine, as in the case of conventional lice combs. For example, the average gap between adjacent teeth can be from about 1 mm to about 10 mm, or from about 2 mm to about 8 mm, or from about 4 mm to about 6 mm.

FIG. 6 is a schematic illustration of system 10 according to embodiments of the invention in which hand-held device 18 comprises a hollow member 44 for removing the parasite by vacuum. It is to be understood that it is not intended to limit the scope of the present invention to the combination illustrated in FIG. 6. Thus, a hollow member 44 can be implemented together with any other configuration, such as, but not limited to, the configurations described above with reference to FIGS. 1-5F.

Member 44 comprises a body portion 46 and a head portion 48, where body portion 46 has an open end 50 adapted to be coupled to a vacuum hose (not shown) and head portion 48 has an opening 52 defining an intake for capturing the parasite.

In use, ultrasound transmitter 16 is activated as further detailed hereinabove for 20 damaging the parasite and member 44 is connected to the vacuum hose for removing the parasite by vacuum. The activation of vacuum is optionally and preferably synchronously with the activation of the ultrasound transmitter. For example, ultrasound radiation can be applied simultaneously with the vacuum. Alternatively, the vacuum and ultrasound radiation can be applied intermittently.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the 30 incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of means "including and limited to".

The term "consisting essentially of means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Embodiments of the present invention have been utilized for killing head lice by ultrasound radiation.

Example 1

Materials and Methods

Living head lice were collected from 35 infected children, ages 4-17. Several trials were performed. For each trial, 50 head lice were selected (10 adult males, 10 adult females and 30 nymphs).

The head lice were placed on a piezoelectric element (Noliac Ceramic or Ferroperm), and 500 µl of distilled water ($dH_2O$) were poured on the lice. The piezoelectric element was activated to emit ultrasound radiation for 3 seconds. The power density at the ultrasound emitting surface of the crystal was set to 0.5 $W/cm^2$.

The head lice were removed from the crystal and washed with normal hair shampoo dissolved in water 1:50 (ARGAN shampoo, Frulatte) for 2 min, and then with water for additional 2 min.

After treatment, head lice were incubated overnight at a temperature of 28° C. and relative humidity of 50%-70%. Mortality was determined after 12-16 hours.

For the control group, the lice were placed in water for 3 seconds without irradiation by ultrasound.

The following procedure was employed for determining the power density. The water temperature was measured before and after 5 minutes of irradiation. The two temperatures were subtracted from each other to obtain the temperature difference T induced by the ultrasound radiation. Then the heat rate Q (energy per unit time) added to the water by the ultrasound radiation was calculated according to the relation $Q=m \cdot C_p \cdot T/t$, where $C_p$ is the specific heat capacity (4.18 J/gr for water), m is the mass of the water and t is the duration of radiation (5 minutes in the present example). To determine the mass of the water, the density of water (0.998 g/ml) was multiplied by the volume of water. The heat rate Q was then divided by the area of the emitting surface of the piezoelectric element, to provide the power density.

Twelve different frequencies were tested: 75 kHz, 140 kHz, 220 kHz, 410 kHz, 560 kHz, 960 kHz, 1200 kHz, 1410 kHz, 1650 kHz, 1800 kHz, 2200 KHz and 2540 kHz.

Results

FIG. 7 is a graph showing the mortality in percentage as a function of the 15 frequency in kHz. As shown, high percentage of mortality was observed at frequency of 1.4-2.54 MHz. A mortality peak was observed at approximately 1.7 MHz.

Example 2

The present Example describes trials performed in accordance with some embodiments of the present invention for investigating the effect of combination of ultrasound radiation and active agents on head lice.

Materials and Methods

Head lice were collected as detailed in Example 1 above. For each trial 100 head lice were selected (25 adult males, 25 adult females and 50 nymphs). In all trials, the frequency of the ultrasound radiation was set to 1.65 MHz.

The following power densities were used output of: 0.065, 0.09, 0.125, 0.25 $W/cm^2$.

The control groups were placed into $dH_2O$ for 2 min with no ultrasonic energy. The following active agents were used for the test groups.

EDTA

EDTA (Ethylenediaminetetraacetic acid, see FIG. 8A) is a strong chelating of divalent metal ions (e.g, $Ca^{2+}$, $Mg^{2+}$, $Zn^{2+}$). EDTA is know to cause nonspecific increase in permeability of Gram negative bacteria and can lyse many such species. Because of its strong complexing ability for most metal ions allows EDTA use for incidents of lead poisoning by the medical profession. Moreover, injection if PbEDTA was found to transfer freely from cell to cell and did not respect the segmental boundary in insect, *Calliphora erythrocephala*[Warner et al., 1982, 28(2):243-52]

Chlorhexidine

Chlorhexidine (CAS Number: 18472-51-0, C9394, Sigma, see FIG. 8B) is a chemical antiseptic and its mechanism of action being membrane disruption. It is effective on both Gram-positive and Gram-negative bacteria, although it is less effective with some Gram-negative bacteria. [World Health Organization, Department of Reproductive Health and Research (1998). "The most common topical antimicrobial". Care of the Umbilical Cord. World Health Organization].

Chlorhexidine has caused extensive damage to the cytoplasmic inner membrane, precipitation or coagulation of protein and nucleic acids [Russell, A. D., and M. J. Day, 1993, Antibacterial activity of chlorhexidine, J. Hosp. Infect. 25:229-238]. Damage also occurs to the outer membrane in gram-negative bacteria and the cell wall in gram-positive cells [Fitzgerald, K. A., A. Davies, and A. D. Russell. 1992. Effect of chlorhexidine and phenoxyethanol on cell surface hydrophobicity of Gram-positive and Gram-negative bacteria. Lett. Appl. Microbiol. 14:91-95].

Chloroxylenol

Chloroxylenol (4-chloro-3,5-dimethylphenol, see FIG. 8C) is an antimicrobial chemical compound used to control bacteria, algae, and fungi in adhesives, emulsions, paints, and wash tanks. It is commonly used in antibacterial soaps such as Dettol and ointments, such as the now discontinued Medicated Vaseline. Its antibacterial action is due to disruption of cell membrane potentials.

Triclosan (Irgasan)

Figure 8A:
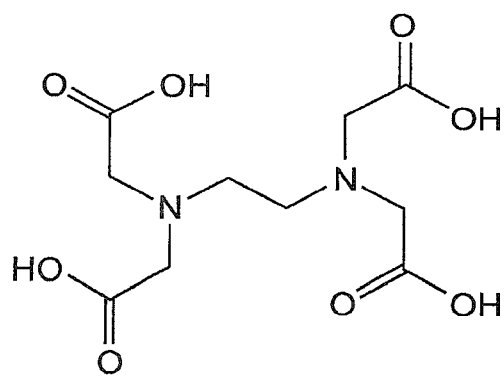
Figure 8B:
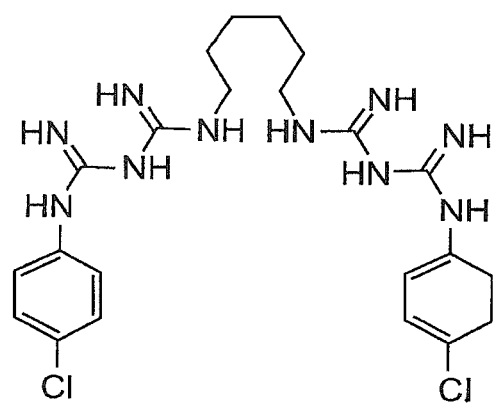
Figure 8C:
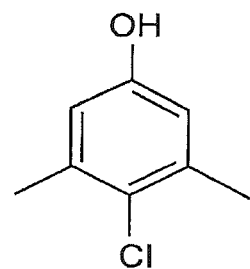
Figure 8D:
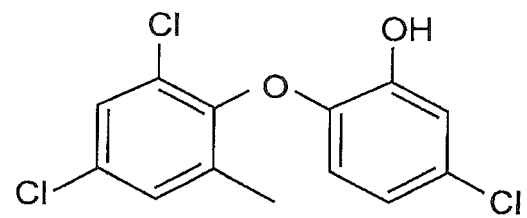

Triclosan (5-chloro-2-(2,4-dichlorophenoxy)phenol, see FIG. 8D), (CAS Number: 3380-34-5, 72779, Sigma) is an antibacterial and antifungal agent. Phenols often show antibacterial properties. Triclosan is present in soaps (0.10-1.00%), deodorants, toothpastes, shaving creams, mouth washes, and cleaning supplies, and is infused in an increasing number of consumer products, such as kitchen utensils, toys, bedding, socks, and trash bags. The commonly used concentration in antiseptic soaps is 1%. Triclosan blocks lipid synthesis by inhibition of the enzyme enoyl-acyl carrier protein reductase, which plays an essential role in lipid synthesis (McMurry, et al., Nature 394:531-532.).

Silica

Silica (SiO2) (CAS Number: 7631-86-9, 420883 Aldrich) is known as a substance that kills insect by absorbing the waxy coating on the insect's body damages their native water balance and causes death by dehydration. Silica is quite a small molecule (60.6 gr/mol). Its small molecular weight assist to penetrate it into head lice body and their eggs. Combination of silica (3%) with $AlO_3$ (0.4%) permits bounding the Aluminum to EDTA. This complex can penetrates into the lice body and caused severe injury to their body. Al is a good conductor to ultrasound waves and even proximity to lice body permit Al becomes conductor nuclei.

The following liquid compositions were prepared: $dH_2O$ (hereinafter composition No. 1), 0.1M EDTA and 1 wt. % SDS (hereinafter composition No. 2), 0.1M EDTA (hereinafter composition No. 3), 1 wt. % Chlorhexidine (hereinafter composition No. 4), 1 wt. % Chlorhexidine and 0.1M EDTA (hereinafter composition No. 5), 3 wt. % Silica (hereinafter composition No. 6), 3 wt. % Silica and 0.1M EDTA (hereinafter composition No. 7), 1 wt. % Chloroxylenol (hereinafter composition No. 8), 1 wt. % Triclosan (Irgasan) (hereinafter composition No. 9), and 1 wt. % Triclosan (Irgasan) and 0.1M EDTA (hereinafter composition No. 10).

Results

FIG. 9 is a graph showing the mortality in percentage as a function of the power density, for various types of active agents. The liquid composition used for each agent is also provided in FIG. 9. The liquid compositions are enumerated from No. 1 to No. 10, as further detailed hereinabove.

As shown, an enhanced mortality (close to 100%) was observed for composition Nos. 6 and 7 and power density above 0.09 $W/cm^2$. Similar results were also obtained with a composition comprising 1 wt. % Silica and 0.1M EDTA, and with a composition comprising 0.5 wt. % Silica and 0.1M EDTA.

Example 3

The present Example describes additional trials performed in accordance with some embodiments of the present invention for investigating the effect of combination of ultrasound radiation and active agents on head lice.

Head lice were collected as detailed in Example 1 above. For each trial 100 head lice were selected (25 adult males, 25 adult females and 50 nymphs). In all trials, the frequency of the ultrasound radiation was set to 1.65 MHz and the power densities were set to 0.25 $W/cm^2$.

The control group was treated as further detailed in Example 2.

Following is a list of the active agents used in the present example, together with their effect on the mortality, when combined with the ultrasound of the present embodiments.

1% Sodium fluorosilicate ($Na_2SiF_6$, CAS Number: 16893-85-9, 71596 Fluka)

1% Barium fluorosilicate ($BaSiF_6$, CAS Number:17125-80-3, 433381 Aldrich)

Each of the above active agents was tested both alone and in combination with ammonium salts, aluminum or magnesium.

All were found to be effective, up to 96%, compared with control group.

Stomach poison, 0.05% Sodium fluoride [NaF, CAS Number:7681-49-4, 47072 Fluka], was found to be effective on head lice with mortality rate of 73%, while increased to 81% combined with EDTA 0.1M.

Carbaryl (CAS Number: 63-25-2, 36856, Fluka see FIG. 10), is known as head lice treatment. This composition is typically applied and maintained on the head for 12 hours. Using 0.04% Carbaryl together with the ultrasound radiation of the present embodiments, resulted in mortality percentage of 78%.

Polyethyleneimine (PEI, CAS Number: 9002-98-6, 03880 Fluka) 4% showed increment of 6% in the mortality percentage, relative to irradiation in the absence of any active agent.

Citric acid 5% showed increased of 8% in the mortality percentage, relative to irradiation in the absence of any active agent.

For any of the compositions in this example, exposing the lice to the composition in the absence of ultrasound radiation for a period of 2 minutes did not show mortality percentage above about 5%.

Example 4

The present Example describes trials performed in accordance with some embodiments of the present invention for investigating the effect of ultrasound radiation on head lice of different sizes and different development stages.

Head lice were collected from 14 different infected children. For each trial 100 head lice were selected. The lice were exposed to the following frequencies: 1410 kHz, 1530 kHz, 1650 kHz, 1800 kHz, 2200 kHz. All the head lice exposed to ultrasound radiation for a period of 3 seconds and at a power density of 0.5 W/cm$^2$.

The stage of development, size and gender of each louse was determined under a binocular (SteREO Discovery.V8, Zeiss), magnification ×20. Head lice that found to be relatively small or large for the respective development stage were not included in the trial.

The results are summarized in Table 1, below. For each stage of development Table 1 lists the size, number of samples, and mortality fraction and percentage for each frequency.

TABLE 1

| Stage | Size [mm] | No. | 1.41 MHz | 1.53 MHz | 1.65 MHz | 1.8 MHz | 2.2 MHz |
|---|---|---|---|---|---|---|---|
| 1$^{st}$ stage nymph | 0.8-1.2 | 20 | 11/20 (55%) | 13/20 (65) | 20/20 (100%) | 20/20 (100%) | 14/20 (70%) |
| 2$^{nd}$ stage nymph | 1.3-1.6 | 20 | 10/20 (50%) | 13/20 (65%) | 20/20 (100%) | 20/20 (100%) | 16/20 (80%) |
| 3$^{rd}$ Stage nymph | 1.6-2 | 20 | 16/20 (80%) | 17/20 (85%) | 20/20 (100%) | 19/20 (95%) | 10/20 (50%) |
| Adult Male | 2-2.6 | 20 | 9/20 (45%) | 14/20 (70%) | 20/20 (100%) | 20/20 (100%) | 14/20 (70%) |
| Adult Female | 2.8-3.4 | 20 | 10/20 (50%) | 16/20 (80%) | 20/20 (100%) | 19/20 (95%) | 18/20 (90%) |
| Total | | 100 | 52% | 73% | 100% | 98% | 78% |

Table 1 demonstrates that the technique of the present embodiments is capable of damaging head lice irrespectively of their stage of development.

The experiments were repeated also for body lice (female adult, about 4 mm in length). Similar results were recorded.

Example 5

The present Example describes trials performed in accordance with some embodiments of the present invention for investigating the effect of a composition which comprises 3 wt. % silica and 0.1M EDTA (composition No. 7 in Example 2, above) when combined with ultrasound radiation on head lice.

Living head lice were collected as further detailed in Example 1. The lice were subjected to either dH$_2$O or composition No. 7. The following frequencies were employed: 560 kHz, 960 kHz, 1090 kHz, 1410 kHz, 1650 kHz, 1800 kHz and 2540 kHz. For each frequency, the power density was varied until mortality percentage of at least 90% were achieved. The results are summarized in Table 2, below and in FIG. 11.

TABLE 2

| | | Power density at which the mortality percentage exceeded 90% | |
|---|---|---|---|
| Exposure time | Frequency | dH$_2$O | 3% silica & 0.1M EDTA |
| 1 sec | 2.54 MHz | 1.5 | 0.35 |
| 1 sec | 1.80 MHz | 0.5 | 0.1 |
| 1 sec | 1.65 MHz | 0.5 | 0.07 |
| 1 sec | 1.41 MHz | 1.55 | 0.2 |
| 1 sec | 1.09 MHz | 2.5 | 0.25 |
| 1 sec | 960 kHZ | >4 | 0.35 |
| 1 sec | 560 kHZ | >5 | >3.5 |

As shown in Table 2 and FIG. 11, the liquid composition allows a considerably reduction in the power density.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device, comprising:
   a base;
   a plurality of teeth extending from the base;
   at least one ultrasound element, wherein the at least one ultrasound element is (a) coupled to at least one of the plurality of teeth, and (b) configured to generate ultrasound waves at an ultrasound wave frequency,
   wherein the device has a sufficient spacing between adjacent ones of the plurality of teeth and the ultrasound wave frequency is a sufficient ultrasound wave frequency so as to result in destroying at least 95% of parasites having a size in a range of between 1.1 mm and 3.4 mm when the device is positioned in proximity to the parasites, wherein the sufficient spacing between adjacent ones of the plurality of teeth is between about 1 mm and about 3 mm, wherein the sufficient ultrasound wave frequency is in a range of between 1.6 MHz and 1.8 MHz.

2. The device of claim 1, wherein the at least one ultrasound element is configured to project the ultrasound waves in a direction that is at an angle of 70° or more to a longitudinal axis of the plurality of teeth.

3. The device of claim 2, wherein the at least one ultrasound element is configured to project the ultrasound waves in a direction that is generally perpendicular to the longitudinal axis of the plurality of teeth.

4. The device of claim 1, wherein the at least one ultrasound element includes at least one ultrasound transducer.

5. The device of claim 4, wherein the at least one ultrasound transducer includes at least one piezoelectric element.

6. The device of claim 1, further comprising a gripping device.

7. The device of claim 1, wherein the at least one ultrasound element includes a plurality of ultrasound elements.

8. The device of claim 7, wherein each of the plurality of ultrasound elements corresponds to one of the plurality of teeth.

9. The device of claim 7, wherein each of the plurality of ultrasound elements includes at least one ultrasound transducer.

10. The device of claim 9, wherein each of the at least one ultrasound transducer includes at least one piezoelectric element.

11. The device of claim 1, wherein the at least one ultrasound element is configured to project the ultrasound waves in a direction that is generally parallel to a longitudinal axis of the plurality of teeth.

* * * * *